United States Patent [19]

Winner

[11] Patent Number: Plant 6,064

[45] Date of Patent: Dec. 22, 1987

[54] VARIETY OF GERANIUM NAMED VICTORIA

[75] Inventor: Blair L. Winner, Lompoc, Calif.

[73] Assignee: Denholm Seeds, Lompoc, Calif.

[21] Appl. No.: 800,974

[22] Filed: Nov. 22, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

A new geranium cultivar is characterized by its compact, upright growth and its brilliant iridescent red flowers.

1 Drawing Figure

BACKGROUND OF THE NEW PLANT

The present invention comprises a new and distinct cultivar of *Pelargonium hortorum* which is a zonal geranium known by the varietal name Victoria (Oglevee No. 887 and Denholm No. 42097-1). The new variety was discovered in a selective breeding program by Mr. Blair L. Winner and is a selection from the crossing of a dwarf early flowering scarlet selection (Denholm No. 34235-9) by "Sunbelt Scarlet" (U.S. Plant Pat. No. 4,039, formerly "Pearlie Mae Red").

The new cultivar was discovered in August of 1982 at Denholm Seeds in Lompoc, Calif., was first asexually reproduced by cuttings by Denholm Seeds at Lompoc, Calif., and has been repeatedly asexually reproduced by cuttings at Oglevee Associates, Inc. in Connellsville, Pa. over a 36 month period. It has also been trial and field tested at Connellsville, Pa. during the summers of 1983, 1984 and 1985. It has been found to retain its distinctive characteristics through successive propagations.

The new cultivar is substantially more compact, a more free basal branching and a darker, more intense red coloring than "Sunbelt Scarlet".

The new cultivar, when grown in a glass greenhouse in Connellsville, Pa. using full light, 60° F. night temperature, 68° F. day temperature and a 71° F. vent temperature and grown in a soilless media of constant fertilizer 275–300 parts per million nitrogen and potassium, has a response time from a rooted cutting to a flowering plant in a 10 cm pot of six weeks.

DESCRIPTION OF THE DRAWING

The accompanying drawing illustrates the new cultivar, the color being as true as possible with color illustrations of this type.

DESCRIPTION OF THE NEW PLANT

The following detailed descriptions set forth the characteristics of the cultivar. The data which define these characteristics were collected from asexual reproductions carried out by Oglevee Associates, Inc. in Connellsville, Pa. The plant histories were taken on plants blossomed under full light in a greenhouse and color readings were taken indoors under 200–220 foot candles of cool, white fluorescent light. Color references are primarily to the R.H.S. Colour Chart of The Royal Horticultural Society of London.

THE PLANT

Classification:

*Botanical.*—*Pelargonium hortorum.*

*Commercial.*—Zonal geraniumm.

Form: Bush; semi-dwarf; free basal branching; compact; flowers close to foliage; free; continuous and early flowering.

Height: 21–25 cm from media surface.

Growth: Free basal branching; compact; semi-dwarf.

Strength: Stands upright without artificial support.

Foliage: Stalked leaf attachment; no leaf zoning.

Leaves:

*Size.*—7.0–9.0 cm across.

*Shape.*—Reniform; cordate base.

*Margin.*—Crenate.

*Texture.*—Pubescent; dull (non-reflective).

*Color.*—Top: Green group 137A; Bottom: Green group 138B.

*Ribs and veins.*—Palmate venation; yellow-green group 145B.

Petioles: Yellow-green group 144A.

Stem:

*Color.*—Yellow-green group 144B.

*Internodes.*—1.0–3.5 cm in length.

THE BUD

Shape: Upright; hemispherical cluster.

Size: 2.0–4.5 cm across.

INFLORESCENCE

Blooming habit: Continuous; upright; semi-double; hemispherical in shape.

Size: 9–11 cm across.

Borne: Umbel; florets on pedicels; pedicels on peduncle.

Florets:

*Form.*—Flat to slightly cupped; with petaloids; ovate.

*Color.*—Top; Red group 40A. Bottom: Red group 40C.

*Petals.*—6–9 in number; separate — not united; margin entire; obovate; palmate venation and insignificant; flat to slightly cupped.

*Size.*—4–5 cm across.

*Texture and appearance.*—Smooth; reflective.

Petaloids:

*Quantity.*—1–5.

*Shape.*—Irregular.

*Color.*—Front: Red group 40A. Back: Red group 40C.

Pedicel:

*Length.*—2.0–2.5 cm in length.

*Color.*—Yellow-green group 144C.

Peduncle: Arise from node; opposed leaf petiole. Yellow-green group 144B. 14–16 cm in length.

Persistence: Moderate. Good foliage persistence.

Disease resistance: Good resistance to Botrytis and Alternaria leaf spots.

Lasting quality: Good heat tolerance.

REPRODUCTIVE ORGANS

Stamens, anthers: Initially purplish-red.

Filaments: Very pale green at base to reddish coloring toward tip same as front of petal; irregular in shape; some petaloid; flat at base and twisted at tip; 4–7 mm in length.

Pollen: Golden brown initially.

Pistils:

*Number.*—1 with 5 part stigma.

*Length.*—8–9 mm.

Stigma: 5 part; color same as front of petal.

Style: 1; purplish-red; 2 mm in length.

Ovaries: 5 mm long; yellow-green; very pubescent (0.1–0.5 mm long); superior.

Fruit: None observed.

The new cultivar is of a compact, upright growth, with brilliant iridescent red flowers.

The new cultivar has been fingerprinted by Dr. Richard Craig and his associates at Penn State University in State College, Pa. The fingerprinting was conducted on a Waters High Performance Liquid Chromatograph equipped with an automatic injection system, dual pumps, solvent programmer, data module, variable wavelength detector, and a $C_{18}$ column. The anthocyanin and flavonol chemical markers utilizing flower petals as an adjunct for cultivar identification were determined.

The anthocyanin and flavonol concentrations of petals just after anthesis of cultivar Victoria florets sampled in April of 1985 are compared with cultivar "Glacier Crimson" (U.S. Plant Pat. No. 5,057) and presented below in Tables 1 and 2. Results are based on the average of multiple tests. It should be noted that changes in environment can influence the biosynthesis.

TABLE 1

| | Anthocyanin Concentration ug anthocyanin 3,5 diglucoside/g fresh wt. | | | | | |
|---|---|---|---|---|---|---|
| Cultivar | Delphinidin | Cyanidin | Pelargonidin | Peonidin | Malvidin | Total |
| VICTORIA | — | 57 | 2994 | 1544 | 329 | 4924 |
| XCR - Bruni | — | 78 | 5251 | 2418 | — | 7747 |

TABLE 2

| | Flavonol Concentration ug/g fresh wt. | | | | | |
|---|---|---|---|---|---|---|
| Cultivar | Qu3-[z] rhagal | Qu3-rut | Qu3-gal | Qu3-glu | Km3-rhagal | |
| VICTORIA | t | 37 | — | 30 | 221 | |
| XCR - Bruni | 11 | 34 | — | t | 307 | |
| Cultivar | Km3-gal | Km3-rut | Km3-xyl | Km3-arab | Km3-rha | Total |
| VICTORIA | 148 | 664 | t | 54 | ND | 1164 |
| XCR - Bruni | 47 | 1257 | 13 | 49 | 185 | 1908 |

[z]Abbreviations: Km = Kaempferol; Qu = Quercetin; arab = arabinoside; gal = galactoside; glu = glucoside; rha = rhamnoside; rhagal = rhamnosylgalactoside; rut = rutinoside; xyl = xyloside. ND = not determined t = trace <10 ug.

I claim:

1. A new and distinct variety of geranium plant substantially as herein shown and described and parts therefor.

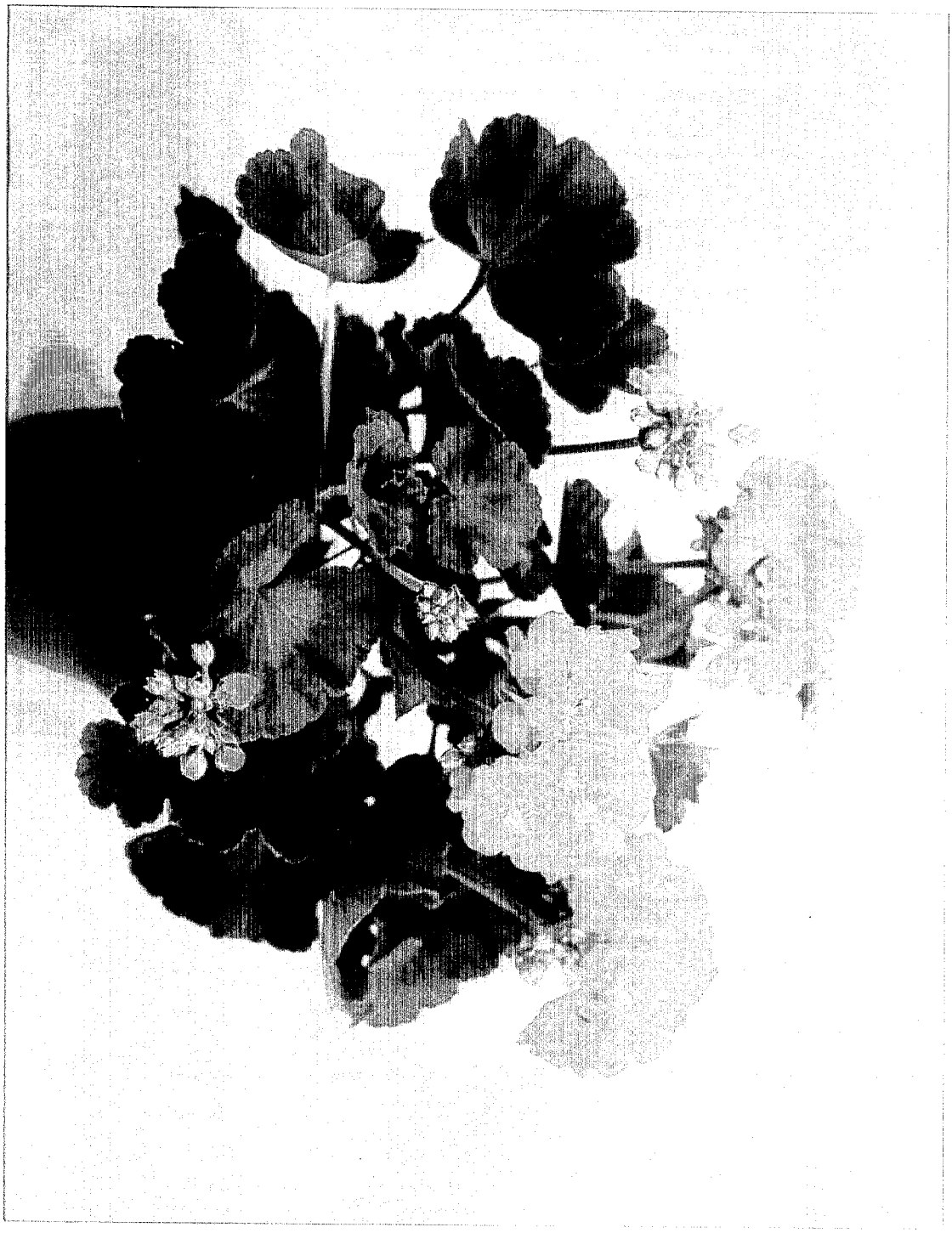

* * * * *